(12) United States Patent
Sawitowski et al.

(10) Patent No.: US 6,697,662 B2
(45) Date of Patent: Feb. 24, 2004

(54) SURGICAL INSTRUMENT

(75) Inventors: Thomas Sawitowski, Essen (DE); Alfons Fischer, Essen (DE)

(73) Assignee: AlCover Surfaces GmbH, Essen (DE)

( * ) Notice: Subject to any disclaimer, the term of this patent is extended or adjusted under 35 U.S.C. 154(b) by 0 days.

(21) Appl. No.: 10/103,570

(22) Filed: Mar. 22, 2002

(65) Prior Publication Data
US 2002/0165578 A1 Nov. 7, 2002

(30) Foreign Application Priority Data

Mar. 23, 2001 (DE) .......................... 101 14 621
May 14, 2001 (DE) .......................... 101 23 442

(51) Int. Cl.⁷ ................................ A61B 5/05
(52) U.S. Cl. ...................... 600/414; 600/410
(58) Field of Search ................. 600/410–429

(56) References Cited

U.S. PATENT DOCUMENTS

| | | | |
|---|---|---|---|
| 4,917,786 A | | 4/1990 | Ehrich |
| 5,096,558 A | | 3/1992 | Ehrich |
| 5,342,283 A | * | 8/1994 | Good ............................ 600/8 |
| 5,565,248 A | | 10/1996 | Plester et al. |
| 5,662,741 A | | 9/1997 | Ehrich |
| 5,744,958 A | * | 4/1998 | Werne .......................... 324/318 |
| 6,261,222 B1 | * | 7/2001 | Schweich, Jr. et al. ........ 600/16 |
| 6,333,971 B2 | * | 12/2001 | McCrory et al. .............. 600/16 |
| 6,447,443 B1 | * | 9/2002 | Keogh et al. .................. 600/37 |

FOREIGN PATENT DOCUMENTS

| DE | 40 06 379 C2 | 4/1991 |
|---|---|---|
| DE | 40 12 048 A1 | 10/1991 |
| DE | 198 11 033 C1 | 8/1999 |
| DE | 199 10 188 A1 | 5/2000 |
| DE | 198 58 578 A1 | 6/2000 |
| DE | 199 48 783 A1 | 8/2000 |

OTHER PUBLICATIONS

"Charakterrollen" ("Character Roll") of Volker Buck and Horst Ehrich, Essener Unikate, Materials Science, vol. 13, Universität GH Essen/Wissenschaftverlag, ISSN 0944–6060 Starting on p. 42.

* cited by examiner

Primary Examiner—Roy D. Gibson
Assistant Examiner—Aaron Roane
(74) Attorney, Agent, or Firm—Nixon Peabody LLP; David S. Safran

(57) ABSTRACT

An MR-compatible surgical instrument is proposed. A simpler, more economic construction is made possible by the use of aluminum or an aluminum compound or alloy as base material, which is covered by a thin barrier layer of an inorganic oxide.

14 Claims, 3 Drawing Sheets

SURGICAL INSTRUMENT

TECHNICAL FIELD

The present invention relates to an operation tool (surgical instrument) that preferably has at least one working section.

RELATED ART

During operations and examinations, location and/or function of the surgical instrument is determined more and more—especially in view of using possible low invasive, i.e. minimally invasive intervention—based on magnetic resonance, whereby, for example, a so-called magnetic resonance tomograph (image) is used. Magnetic resonance—here abbreviated as MR—is, thus, used here for the illustration of spatial relationships in a body, for example the location of tissues, organs and/or surgical instruments, wherein a relatively strong magnetic field is applied and substances and materials can be differentiated due to the different magnetic characteristics. Operations and examinations in which MR is used supportively, e.g. as a control function or as a guide, for example to the correct location of an instrument, will be abbreviated here as well to "MR-guided and/or MR-based".

In order to be able to use MR, the use of MR-compatible substances for surgical instruments or their working sections is necessary. When using conventional materials, such as stainless steel, such artifacts (defect image) result that MR makes no or only an insufficient (figurative or spatial) resolution possible.

DE 198 11 033 C1 discloses a surgical instrument and method for its production. In order to reduce the weight of the surgical instrument, it is provided that it consists entirely or in essential parts of aluminum or an aluminum alloy and that the surface of the aluminum or the aluminum alloy is provided with a thin aluminum-nitride layer of, in particular, 1 to 10 $\mu$m. It has been seen, for example, that such instruments produce practically no artificial signals (artifacts) in magnetic resonance tomography (imaging). The aluminum-nitride layer is preferably achieved by surface-melting the parts consisting of aluminum or an aluminum alloy by means of laser radiation in a nitrogen atmosphere. This is very elaborate. The aluminum-nitride layer is relatively thick, so that the risk of an undesired peeling or splitting exists, in particular in the case of intense strain on the surgical instrument.

DE 198 11 033 C1 provides only an aluminum-nitride layer and, because of this, accomplishes that contact of the metallic aluminum to the surroundings is impossible. However, no statement is made about to what extent the aluminum-nitride layer is impermeable for aluminum ions or bodily fluids.

Consequently, there is a need to provide an operation tool or surgical instrument that is suitable for MR-guided or MR-based operations and examinations, however, one that can be produced more easily and economically and can effectively prevent a peeling off of the aluminum in the body.

SUMMARY OF THE INVENTION

The present invention is based on the object of providing a surgical instrument that is suitable for MR-guided or MR-based operations and/or examinations, in particular on human or animal bodies, wherin the surgical instruments can be produced more easily and more economically with very good mechanical characteristics.

A fundamental idea of the invention is to use aluminum or an aluminum compound preferably consisting primarily of aluminum or an aluminum alloy or a mixture thereof as base material or main part of the surgical instrument or at least for its working section and providing a barrier layer of an inorganic oxide.

In the present invention, the term "surgical instrument" should be understood primarily as device or instrument that can be used in particular in an operation or examination, in particular on human or animal bodies, namely, preferably, inserted and/or, for example, is used to have an effect on bodily tissue. In a broader sense, however, general surgical instruments and other instruments, devices and aides that are used for operations and/or examinations and, in particular, come into contact with the respective body should also be understood under this term.

In the present invention, "working section" should be understood as at least a part of the surgical instrument that is essential for the defined function of the surgical instrument and/or primarily comes into contact with or is inserted in the body being operated and/or examined. In this case, it is particularly a matter of a relatively small part in the area of the respective operation or examination location. The surgical instrument can, for example, have further sections or parts, such as a handle or the like, that also comes into contact with the body or is inserted therein.

Tests have shown that aluminum is at least partially invisible in a magnetic resonance tomograph (image). Thus, with the use of MR, the artifacts that are otherwise generally present in the case of metals do not emerge.

In view of MR-compatibility, it can suffice to have only one working section, for example a canula, a scalpel, a hook, a clamp, a bracket or the like located immediately at the respective operation location, which consists at least essentially of the proposed base material. However, the entire surgical instrument is preferably manufactured at least essentially of the proposed base material.

However, as an alternative, the base material can also form only a coating or layering on another carrier material, wherein the surgical instrument or its active area can consist essentially of the carrier material, i.e. of another material.

Furthermore, the base material, in particular the entire surgical instrument, is covered by a barrier layer—at least on open surface areas or surface areas accessible to bodily fluids/tissues. The barrier layer is impermeable for aluminum, aluminum ions and bodily fluids. This prevents aluminum ions, which are thought to be harmful, from dissolving in the body.

The amorphous barrier layer of an inorganic oxide is very simple and can correspondingly be economically produced, e.g. by oxidizing the aluminum of the base material.

Furthermore, a very high quality impermeability can be achieved even at a low thickness with an inorganic oxide, in particular silicon dioxide or aluminum oxide, so that the barrier layer can be formed more thinly. This allows, depending on the method, a low layering time, i.e. a fast and therewith economical formation of the barrier layer.

Ripping or flaking of the barrier layer can be countered by the possible thin formation.

A preferred embodiment provides that the working section or the surgical instrument having an MR-visible material is marked. In this case "to mark" means that the material is provided, at points or spread out, in a sufficient amount in order to make the working section or the entire surgical instrument visible without creating the undesired artifacts (defect image or covering of other areas) of MR.

The MR-visible material, such as a precious metal, heavy metal or iron can be immediately added to the base material in a suitable amount, wherein the aluminum can, for example, be "made impure" for marking with an adequate amount. An aluminum alloy cannot be taken into consideration in this case, since the amount of material to which aluminum is to be added is too low.

However, the MR-visible material for marking is preferably not directly integrated in to the base material, but rather provided in or on the barrier layer. For example, the MR-visible material can be contained in the barrier layer material and/or can be incorporated in the hollow spaces formed in the barrier layer.

BRIEF DESCRIPTION OF THE DRAWINGS

Further characteristics, features, aspects and advantages of the present invention are described in more detail for two embodiments using the drawing. It shows FIG. 1 a schematic representation of a surgical instrument according to the invention.

DETAILED DESCRIPTION OF A PREFERRED EMBODIMENT

Figure 1:
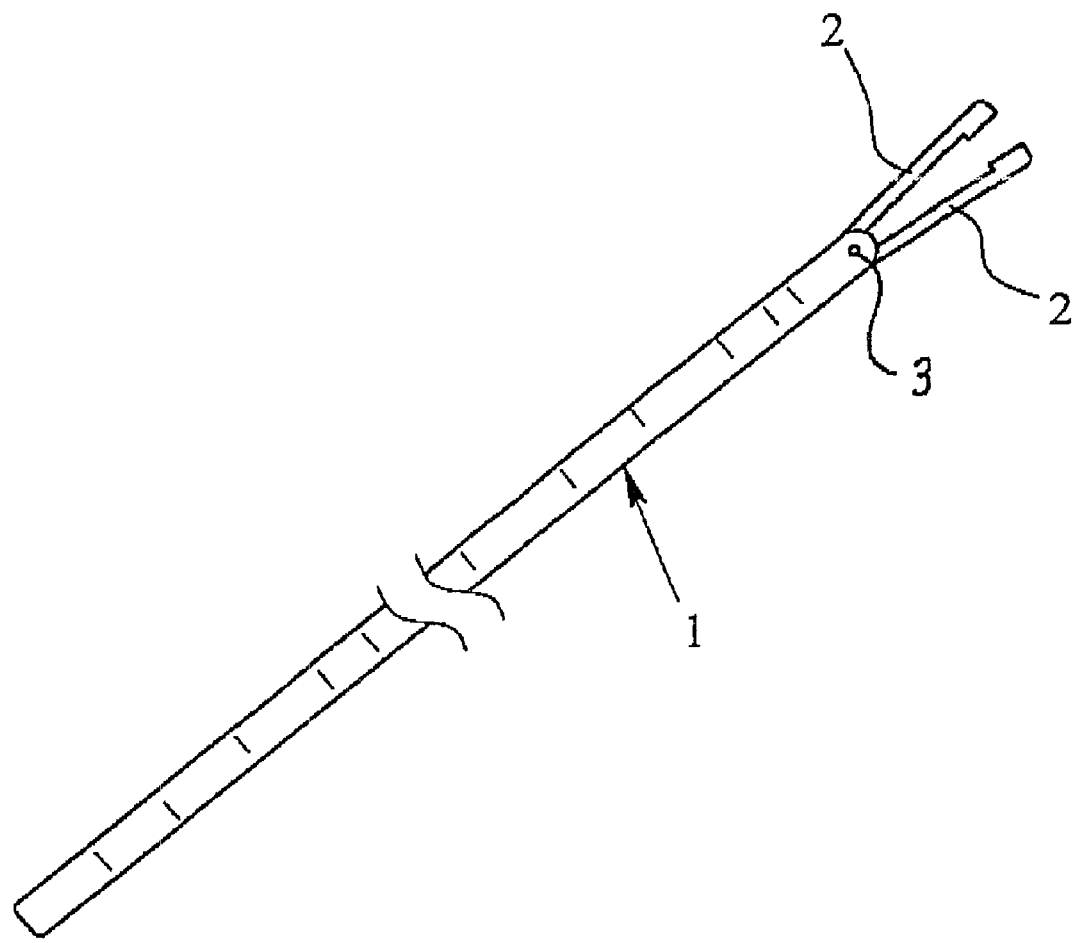

FIG. 1 shows a surgical instrument 1 according to the invention in a manner as described in the introduction. The preferred embodiment deals with a forceps-like instrument or tool. As already described, it can be a matter of any sort of instrument, technical aide or tool for examination or operation on human or animal bodies.

The surgical instrument 1 has preferably at least one working section 2, here, there are two working sections 2 joined via a joint 3. Here, the working sections 2 form a forceps-like gripping-, retaining- and/or cutting element. The term "working section" is, however, not limited to a singular part, but concerns, moreover, on the one hand, a multiplicity of parts or on the other hand, a section or area of a one-piece part.

As already pointed out in the case of the working section 2, it is, in particular, a matter of the forward or relevant area of the surgical instrument 1 whose surroundings should be invisible or visible, with corresponding markings, through MR.

Figure 2:
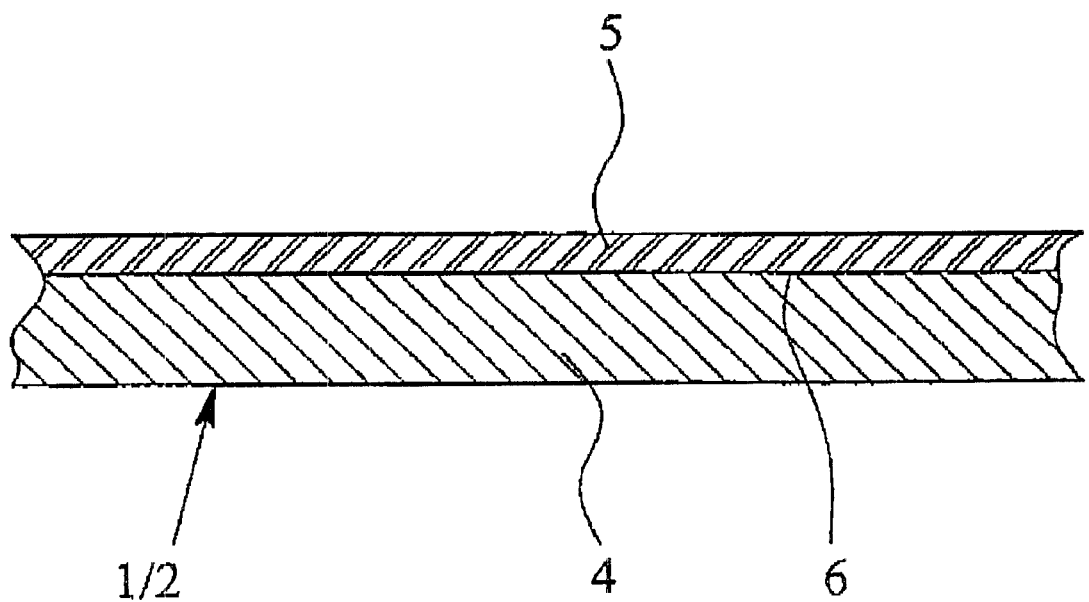
FIG. 2 a sectional representation of the schematic construction of the surgical instrument.

FIG. 2 shows an enlarged section of the material construction according to the invention that is not to scale. The material construction is provided at least for the working section 2 of the surgical instrument 1 or, if necessary, for the entire surgical instrument 1. For the sake of simplicity, reference will be made only to the surgical instrument 1 in the following, even when the corresponding embodiment holds good for at least one working section 2 of the surgical instrument 1 or the entire surgical instrument 1.

Figure 3:
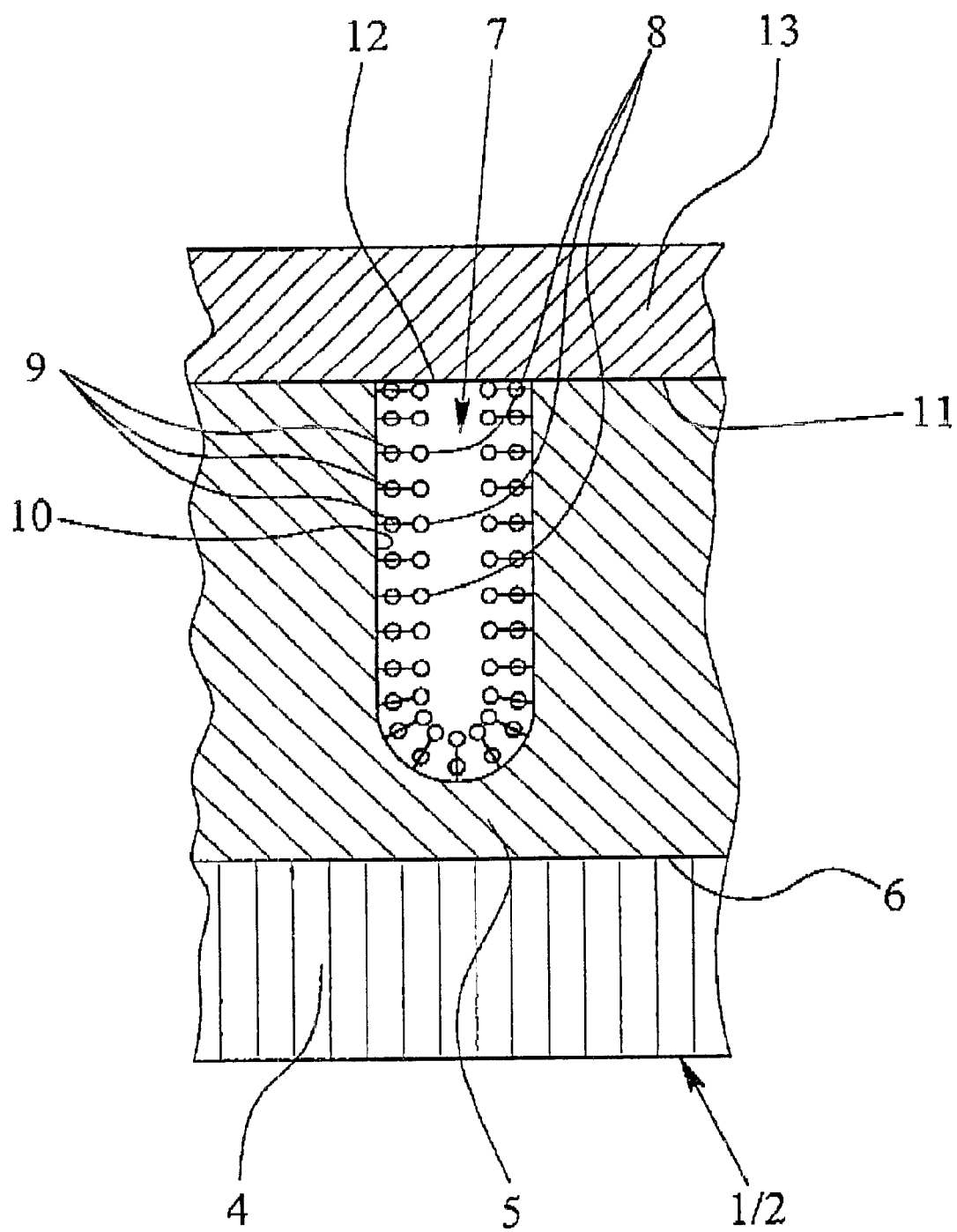
FIG. 3 a further enlarged, schematic representation of a possible layer construction according to FIG. 2.

The surgical instrument 1 consists preferably of at least essentially one base material as implied in FIG. 3. In particular, FIG. 3 shows only a partial section of the material of the surgical instrument 1 or of an working section 2.

The base material 4 is preferably covered by a barrier film 5 on its surface, at least on its surface areas 6 that are uncovered and/or accessible to bodily fluids or tissues.

The base material 4 consists, at least essentially, of aluminum, an aluminum compound, an aluminum alloy and/or mixtures thereof, in particular of relatively pure aluminum. Preferably, the base material 4 consists of at least a 95 mass-%, preferably 97 mass-%, of aluminum, in particular a corresponding aluminum alloy.

Therewith, the MR compatibility of the base material 4 results, as already mentioned.

The optionally provided barrier film 5 is relatively thin and preferably amorphously formed. Thereby a good or acceptable flexibility results having a particularly good adhesion to the base material 4 in order to prevent the barrier layer 5 from peeling away.

Preferably, the barrier layer 5 is at least essentially uniformly formed. In particular, the average thickness is 10 to 200 nm, preferably 20 to 100 nm and in particular about 50 nm.

The barrier layer 5 is preferably formed so that it is impermeable to the base material 4, ions formed therefrom and/or bodily fluids or other bodily materials. In this way, the peeling away of the base material can be prevented in the body.

For the formation of the barrier layer 5, the base material is plasma coated, i.e. the barrier layer is applied using a plasma method. The material to be applied, in this case silicon, is vaporized in a vacuum and reacts under the addition of oxygen on the surface of the base material 4 forming a strongly adhesive oxide layer that is predominantly amorphous and, thus, flexible.

As examples for the possibilities of the formation of the barrier film, i.e. a film/coating, in particular relating to the application of a silicon dioxide film, U.S. Pat. Nos. 4,917,786, 5,096,558, 5,565,248 and 5,662,741 are referred to whose content is hereby cited as additional reference material. However, the application is not limited to a pure plasma method. Moreover, other methods can be used, in particular plasma supported methods such as the plasma supported PVD method or the plasma supported CVD method can also be used, as disclosed in the article "Charakterrollen" ("Character Rolls") of Volker Buck and Horst Ehrich, Essener Unikate, materials science, Volume 13, Universität GH Essen/Wissenschaft-verlag, ISSN 0944-6060 starting on page 42. In addition, the above-mentioned journal is given as a citation in view of layering methods and usable materials and in view of usable biocompatible materials.

Preferably, the barrier film 5 consists of at least essentially one half-metal oxide, in particular silicon dioxide. Silicon dioxide has an excellent biocompatibility as the most common inorganic bond, i.e. is optimally compatible for the body. An adequately thick or impermeable barrier layer 5 can be formed with silicon dioxide.

Adequate flexibility and adhesion on the base material 4 or the surface areas 6 to be covered is also achieved in the case of the preferably provided amorphous formation.

It is possible, through a relatively low thickness of the barrier layer 5, to use almost any desired material that is not MR compatible per se for the barrier layer. Due to the low total amount that is needed for the formation of the barrier layer 5, a total sufficient MR compatibility remains. If necessary, the barrier layer 5 can simultaneously represent a desired "marking", i.e. effect that a surgical instrument 1 is still visible by means of MR—i.e. for example using magnetic resonance tomography (imaging)—, which is not the case in the sole use of high quality, pure aluminum.

Alternatively, the barrier layer 5 can also consist of other materials, in particular at least essentially of aluminum oxide or titanium dioxide. A formation of aluminum dioxide is advantageous since, in this case, the base material 4—at least insofar as it concerns aluminum—needs only be oxidized on its surface. This results in particular through electrolytic oxidation (anodization), wherein a sufficiently thick or impermeable barrier layer 5 having the desired characteristics—adequate flexibility, amorphous construction—can be achieved.

In the following, a further construction or variation of the embodiment for MR-visible marking is explained in more detail using the sectional enlargement according to FIG. 3.

In the variation of the embodiment shown in FIG. 3, hollow spaces 7 are formed in the barrier layer 5—for example through respective anodization, in particular in the use of aluminum oxide as the material for the barrier layer 5—for the assimilation of a MR-visible material 8.

The MR-visible material 8 can be formed, for example, using metal, in particular using a precious metal or a heavy metal. If necessary, the material 8 can be bound using a schematically indicated bond partner 9 on the walls 10 of the hollow space 7.

In the embodiment, the hollow spaces 7 are formed with an open structure to the outside or surface 11 of the barrier layer 5, i.e. have openings 12. If necessary, the openings 12 or the surface 11 can be covered by a cover layer 13, e.g. of gold.

In the formation of the hollow spaces 7 in the barrier layer 5, said hollow spaces 7 preferably do not extend through the entire thickness of the barrier layer 5 in order to retain the resistant effect or barrier effect of the barrier layer 5, i.e. to ensure the desired impermeability.

As already mentioned, the MR-visible material 8 can be incorporated in another manner, if necessary in the base material 4 and/or the barrier layer 5, or if required, mixed with each individual material.

INDUSTRIAL APPLICABILITY

The present invention is provided in particular for surgical instruments, which are economically produced, that can be used for MR-guided or MR-based operations and examinations, in particular on an open magnetic resonance tomograph (image).

What is claimed is:

1. Surgical instrument for MR-guided or MR-based operations or examinations, in particular on human and/or animal bodies, having working section that at least essentially consists of a metallic base material, wherein the base material is at least one of aluminum, an aluminum compound, an aluminum alloy and/or mixtures thereof, wherein the base material is covered by a barrier layer at least on surface areas that are open and/or accessible for bodily fluids or bodily tissues, wherein the barrier layer is impermeable for aluminum, aluminum ions and bodily fluids, and wherein the baffler layer consists at least essentially of an inorganic oxide and is formed amorphously for achieving adequate flexibility and adhesion on the base material.

2. Surgical instrument according to claim 1, wherein the entire surgical instrument consists at least essentially of the base material.

3. Surgical instrument according to claim 1, wherein the base material consists of at least 97 mass-%, of aluminum.

4. Surgical instrument according to claim 1, wherein the baffler layer is made of at least one of aluminum oxide, titanium dioxide and/or silicon dioxide.

5. Surgical instrument according to claim 1, wherein the working section or the base material is marked with an MR-visible material.

6. Surgical instrument according to claim 5, wherein the MR-visible material is provided or adapted or arranged for determining the location of the surgical instrument during operations or examinations by means of MR.

7. Surgical instrument according to claim 5, wherein the MR-visible material contains or consists of a half-metal or metal.

8. Surgical instrument according to claim 5, wherein the MR-visible material is located in the base material and/or the barrier layer.

9. Surgical instrument according to claim 8, wherein the MR-visible material is located in hollow spaces in the barrier layer formed preferably using electrolytic oxidation.

10. Surgical instrument according to claim 5, wherein the MR-visible material contains or consists of a precious metal or heavy metal.

11. Surgical instrument according to claim 1, wherein the barrier layer has an average thickness of 10 to 200 nm.

12. Surgical instrument according to claim 1, wherein the base material consists at least essentially of aluminum and the base material is oxidized in the area of the surface to form the barrier layer.

13. Surgical instrument according to claim 12, wherein the base material is electrolytically anodized to form the barrier layer.

14. Surgical instrument according to claim 1, wherein the base material consists of at least 98 mass-% of aluminum.

* * * * *